United States Patent [19]
Moose, Jr.

[11] 4,196,723
[45] Apr. 8, 1980

[54] DUAL FENESTRATED SURGICAL DRAPE WITH A FLAP CAPABLE OF COVERING AND ISOLATING EITHER FENESTRATION

[75] Inventor: Lawrence A. Moose, Jr., Memphis, Tenn.

[73] Assignee: The Procter & Gamble Company, Cincinnati, Ohio

[21] Appl. No.: 949,239

[22] Filed: Oct. 6, 1978

[51] Int. Cl.² ............................................. A61B 19/06
[52] U.S. Cl. ............................................... 128/132 D
[58] Field of Search ........................... 128/132 D, 292

[56] References Cited
U.S. PATENT DOCUMENTS

| | | | |
|---|---|---|---|
| 1,724,443 | 8/1929 | Wheeler | 128/132 D |
| 3,799,161 | 3/1974 | Collins | 128/132 D |
| 3,910,268 | 10/1975 | Miller | 128/132 D |
| 3,926,185 | 12/1975 | Krzewinski | 128/132 D |
| 3,942,523 | 3/1976 | Rudtke | 128/132 D |
| 4,027,665 | 6/1977 | Scrivens | 128/132 D |

Primary Examiner—Lawrence W. Trapp
Attorney, Agent, or Firm—Frost & Jacobs

[57] ABSTRACT

A surgical drape having first and second fenestrations formed therein. A flap is hingedly affixed to the surgical drape between the first and second fenestrations. The flap is shiftable between a first position in which it covers and isolates the first fenestration and a second position in which it covers and isolates the second fenestration. Means may also be provided to secure the flap in either or both of the its first and second positions.

14 Claims, 2 Drawing Figures

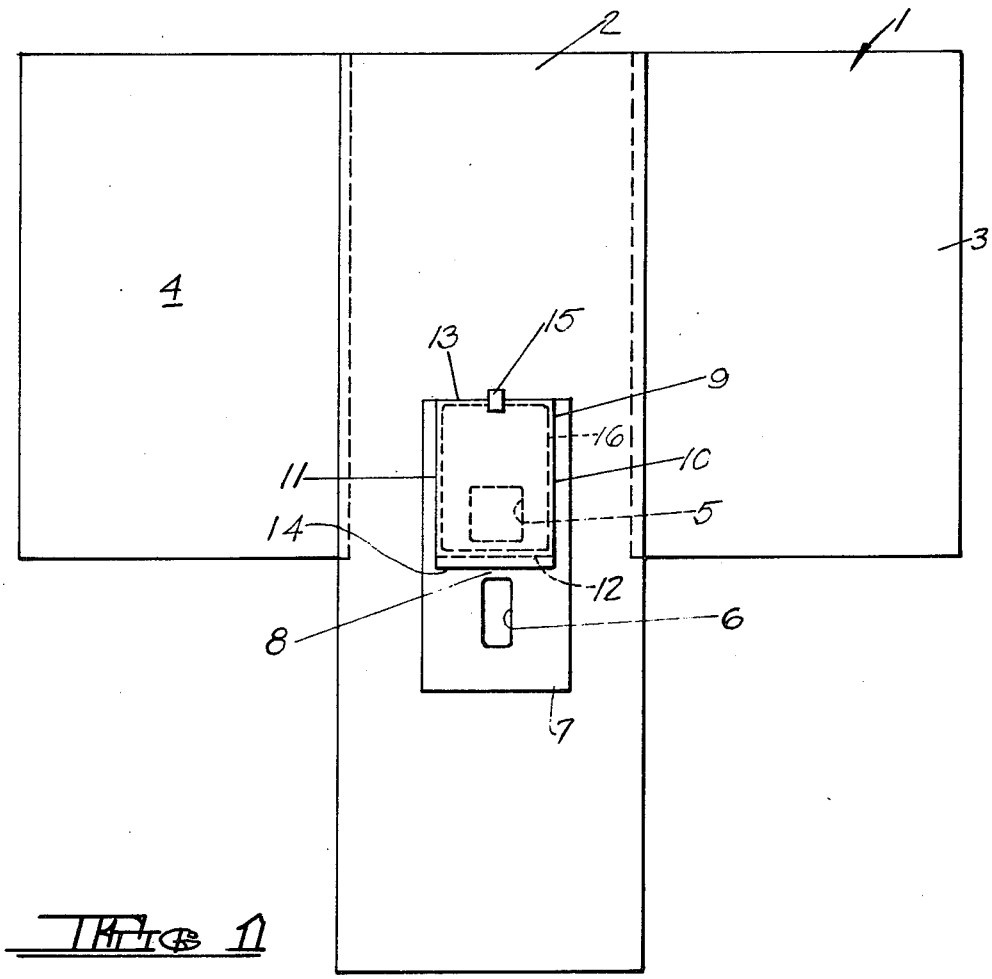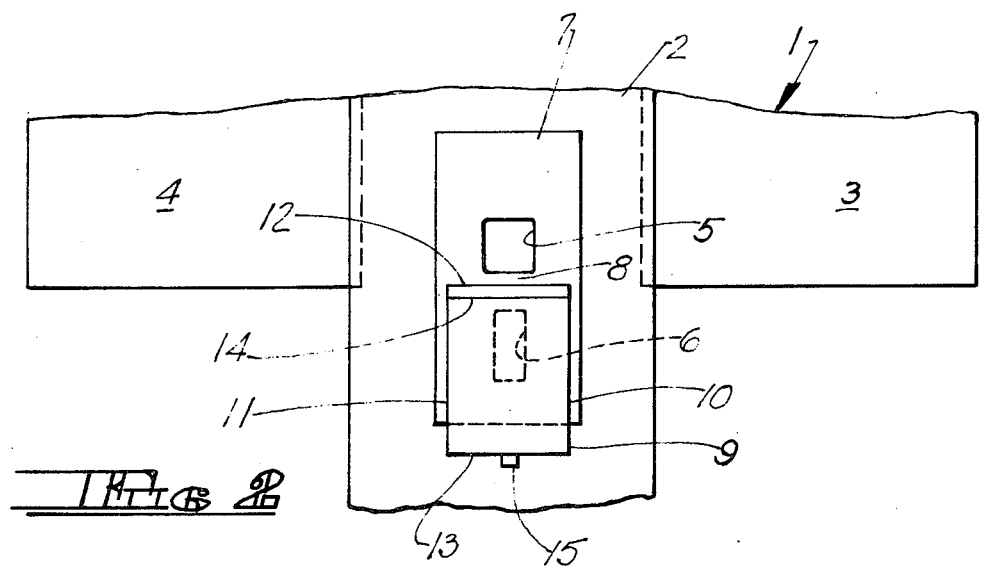

DUAL FENESTRATED SURGICAL DRAPE WITH A FLAP CAPABLE OF COVERING AND ISOLATING EITHER FENESTRATION

TECHNICAL FIELD

The invention relates to a surgical drape, and more particularly to a dual fenestrated surgical drape provided with a flap hingedly attached to the surgical drape between the fenestrations and shiftable between positions in which it covers and isolates either fenestration.

BACKGROUND ART

While the teachings of the present invention are applicable to surgical drapes for any surgical procedure requiring two fenestrations in reasonably close proximity to each other and in which it is desirable at different times to cover and isolate one or the other of the fenestrations, the surgical drape of the present invention is particularly well suited for those well known surgical procedures requiring both abdominal and perineal entry. For purposes of an exemplary showing, the surgical drape of the present invention will be described in its application as a laparoscopy drape. While the drape may be made of any appropriate reusable or disposable material, it will (again for purposes of an exemplary showing) be described as a single-use disposable laparoscopy drape.

Prior art workers have devised numerous surgical drapes and sheets with multiple fenestrations for use in various types of surgical procedures. U.S. Pat. No. 3,799,161, in the name of Robert F. Collins, issued Mar. 26, 1974 and U.S. Pat. No. 4,027,665 in the name of George W. Scrivens, issued June 7, 1977, are exemplary of prior art patents teaching surgical drapes with multiple fenestrations.

Disposable surgical drapes are also well known in the art. In U.S. Pat. No. 3,942,523 in the name of Helen T. Rudtke, issued Mar. 9, 1976, there is taught a disposable surgical drape specifically for use in surgical procedures such as laparoscopy procedures, the surgical drape being provided with a pair of aligned fenestrations.

Prior art workers have also developed various types of removable closure members or covers for surgical drape fenestrations. The above mentioned U.S. Pat. Nos. 3,799,161 and 4,027,665 describe fenestration cover means. Such cover means, however, are each associated only with a single fenestration and are generally not intended to be replaced, once opened and removed.

Surgical drapes have also been devised having a type of flap means. Such surgical drapes are provided with a fenestration, located generally inwardly of the perimeter of the drape, and a slit which extends from the perimeter of the drape to the fenestration. In the use of such drapes, an extremity (such as a leg or the like) of the patient is caused to extend through the fenestration, the drape being placed about the extremity by virtue of the slit. The flap-like means on the drape is then used to close the slit, but does not cover the fenestration. Examples of such drapes are taught in U.S. Pat. No. 3,910,268, in the name of Shirley A. Miller, issued Oct. 7, 1975, and U.S. Pat. No. 3,926,185 in the name of Henrietta K. Krzewinski, issued Dec. 16, 1975.

The present invention is directed to surgical drapes for surgical procedures requiring two fenestrations in the drape located reasonably close together (as for example a fenestration for the abdominal area and a fenestration for the perineal area) and in which it is desirable or necessary during the surgical procedure to cover and isolate one or the other of the fenestrations. Heretofore, this has been accomplished through the use of surgical drape towels which require unfolding, placement and fastening. The present invention contemplates the provision of a flap, hingedly affixed to the surgical drape between the fenestrations and shiftable so as to be capable of covering and isolating either fenestration. This greatly enhances patient protection during surgery. Furthermore, the ease and speed of draping are improved because the flap is already in place on the drape and does not require unfolding, placement and fastening as does a surgical drape towel. Since the hinged flap is securely fastened to the drape, the possibility of slippage, as in the case of a drape towel, is eliminated.

DISCLOSURE OF THE INVENTION

In accordance with the present invention there is provided a surgical drape having first and second fenestrations formed therein. A flap is hingedly affixed to the surgical drape between the first and second fenestrations. The flap is shiftable between a first position in which it covers and isolates the first fenestration and a second position in which it covers and isolates the second fenestration.

The surgical drape may be either reusable or disposable. The flap may be provided with one or more adhesive tabs or the like to maintain it in either or both of its first and second positions. The surgical drape may also be provided with a fenestration control insert, as will be described hereinafter.

BRIEF DESCRIPTION OF THE DRAWINGS

FIG. 1 is a plan view of the surgical drape of the present invention illustrating the flap in its first position covering the first fenestration of the surgical drape.

FIG. 2 is a fragmentary plan view of the surgical drape of FIG. 1 illustrating the flap in its second position covering the second drape fenestration.

DETAILED DESCRIPTION OF THE INVENTION

FIG. 1 is a plan view of an exemplary laparoscopy drape of the present invention. The drape is generally indicated at 1 and the Figure illustrates the outer or upper side of the drape (i.e. that side facing the surgeon). The drape comprises a central, elongated, substantially rectangular panel 2 and two laterally extending, rectangular panels 3 and 4 of lesser length. Those longitudinal edges of panels 3 and 4 adjacent panel 2 are overlapped thereby by a short distance and are permanently affixed thereto as by sewing, adhesive bonding, or the like, depending upon the material from which panels 2 through 4 are made.

The panels 2 through 4 may all be made of the same material, if desired. If the laparoscopy drape is intended to be reusable, the panels 2 through 4 may be made of any of the well known woven materials suitable for use in a surgical environment. If the laparoscopy drape is intended to be a single-use, disposable drape, the panels 2 through 4 may be made of any appropriate nonwoven fabric or nonwoven composite fabric suitable for use in a surgical environment. Appropriate disposable materials for this purpose are well known and in common use.

During a laparoscopy procedure, the patient will normally be located on an appropriate operating table with the patients legs held in elevated position by stirrup means. Panel 2 of the laparoscopy drape is so sized as to cover the majority of the patient's body, extending between the patient's legs and downwardly over the adjacent end of the operating table. Laterally extending flaps 3 and 4 will cover the patient's sides and will extend downwardly along either side of the operating table.

The central panel 2 is provided with a first substantially rectangular fenestration 5 so located as to overlie the appropriate abdominal area of the patient. The central panel 2 is provided with a second, substantially rectangular fenestration 6 appropriately positioned to overlie the perineal area of the patient. The fenestrations 5 and 6 are aligned, sharing the same longidutinal center line.

Central panel 2 may also be provided with a rectangular reinforcing patch 7. The patch 7 is of such size as to surround fenestrations 5 and 6 and to cover that area of the drape immediately thereabout. The reinforcing patch 7 and the provision of rounded corners for fenestrations 5 and 6 will prevent tearing of the surgical drape in this area and particularly that portion 8 of the surgical drape 1 between fenestrations 5 and 6. Should the portion 8 become torn or broken, redraping of the patient would be necessary to prevent cross contamination. The patch 7 may be so selected as to impart to that portion of the drape containing fenestrations 5 and 6 those desired properties relating to liquid absorption, liquid strikethrough and the like, as is well known in the art.

The surgical drape 1 is provided with a flap 9. The flap 9 may be made of the same material used to make panels 2, 3 and 4 and is illustrated as being substantially rectangular. The flap 9 is illustrated as having longitudinal edges 10 and 11 and end edges 12 and 13. The end edge 12 of flap 9 is hingedly secured to that portion 8 of surgical drape 1 and reinforcing patch 7 between fenestrations 5 and 6. The hinged attachment may be accomplished in any appropriate manner and should be along a line substantially perpendicular to the common longitudinal center line of fenestrations 5 and 6.

One method of attaching flap 9 to the surgical drape 1 is illustrated in FIGS. 1 and 2. The flap 9 has a strip of adhesive laid thereon adjacent end edge 12. In this manner, the flap 9 is adhesively affixed to the patch 7 with the result that the flap 9 will pivot or swing about a fold line indicated in FIGS. 1 and 2 at 14. The line 14 is not a preformed fold line in flap 9, but rather it represents one longitudinal boundary of the glue stripe, the end edge 12 of the flap constituting the other longitudinal boundary of the glue stripe. The glue stripe, itself, is not visible in FIGS. 1 and 2 since it is located between the edge portion of flap 9 and the reinforcing patch 7.

In FIG. 1, the flap 9 is illustrated in what may be, for purposes of this description, designated as its first position wherein it is folded upon itself where attached to the reinforcing patch and extends over and isolates the first or abdominal fenestration 5. This first position of flap 9 is the position in which the flap will be located during the folding, packaging and sterilizing procedures for the drape and the flap will normally remain in this position during the initial portion of the laparoscopy surgical procedure. To assure that flap 9 remains in this first or initial position, its end edge 13 may be provided with a tape tab 15 removably adhered to the surgical drape panel 2, as shown in FIG. 1.

The surgical drape 1 may be provided with a fenestration control insert shown in broken lines at 16 in FIG. 1. The fenestration control insert comprises a rectangular insert of any appropriate material for use in a surgical environment and capable of withstanding the same sterilization procedure to which the surgical drape is subjected prior to use. The fenestration control insert 16 is located between the reinforcing patch 7 and the flap 9 and protects the flap 9 or any other part of the surgical drape from contamination by the skin of the patient at the position of fenestration 5 during the draping procedure and the like.

FIG. 2 illustrates the flap 9 in its second position wherein it covers and isolates the second or perineal fenstration 6. To shift flap 9 from its first or initial position shown in FIG. 1 to its second position shown in FIG. 2, it is only necessary for the surgeon to grasp tape tab 15, disengage it from panel 2 of the drape, and using it as a sort of handle, shift the flap 9 about fold line 14 to its second position illustrated in FIG. 2. At this point, the fenestration control insert 16 may be removed and discarded.

The laparoscopy drape 1 will be folded in such a way as to expedite the draping procedure, packaged and subjected to appropriate and well known sterilizing procedures. In use, the drape will be appropriately applied to the patient during the draping procedure. The patient's legs will normally be draped with disposable leggings, well known in the art and not constituting a part of the present invention. The hinged attachment of flap 9 to portion 8 of the surgical drape not only additionally reinforces this portion of the surgical drape, but also (in combination with tape tab 15) will assure that the flap is securely held in its first position covering and isolating the first or abdominal fenestration 5. Since the flap 9 is already in place, it is not necessary for the surgeon (or a member of the surgical team) to unfold, place and fasten a drape towel over the fenestration 5. As a result, the draping procedure is considerably easier and faster.

From the time the drape is positioned on the patient until the vaginal examination is complete, the flap 9 remains in its first or initial position over the abdominal fenestration 5. When the surgeon prepares for the abdominal incision, the flap may be lifted by adhesive tab 15 and subsequently allowed to fall over the perineal fenestration 6, thus isolating from the surgical field the fenestration 6 and any protruding surgical instrument used for uterine manipulation. Such a surgical instrument may thereafter be grasped using the flap 9, if desired. Once the flap 9 has been shifted to its second position, the fenestration control insert 16 may be removed and discarded. The abdominal fenestration 5 is then exposed and the laparoscopy procedure may then be continued and completed.

Excellent results have been achieved utilizing laparoscopy drapes made in accordance with the teachings of the present invention. In a working embodiment, the central panel 2 of the laparoscopy drape measured 243.8 cm by 80 cm. Laterally extending panels 3 and 4 were each 134.6 cm by 91.4 cm. The panels 2, 3 and 4 were made of a tissue laminate comprising two outside layers of cellulosic tissue and an intermediate layer of latex impregnated polyester. Such nonwoven fabic is taught in common owned copending application Ser. No. 741,640, filed Nov. 15, 1976 in the names of Larry L.

Lafitte and James B. Camden and entitled *QUIET, STRONG CLOTH-LIKE TISSUE LAMINATE*. The central panel 2 lapped the adjacent longitudinal edges of laterally extending panels 3 and 4 by about 2.5 centimeters and these lapped edge portions of laterally extending panels 3 and 4 were permanently affixed to central panel 2 by a compounded aqueous resin emulsion adhesive sold under the designation NW-15H by Chemionics Company, a division of Adhesive Incorporated, of Fairlawn, N.J.

The reinforcing patch 7 measured 76.2 cm by 38.1 cm. The reinforcing patch 7 constituted a laminated material comprising outer carded rayon webs and an intermediate polethylene sheet. This material is sold by the Minnesota Mining and Manufacturing Company of St. Paul, Minn. under the trademark Isodrape. The reinforcing patch 7 was overall adhered to the upper surface of central panel 2 by an acrylic latex adhesive.

The first or abdominal fenestration 5 measured about 15.5 cm by 12.5 cm. The second or perineal fenestration 6 measured about 15 cm by about 7.5 cm. The width of drape portion 8 between fenestrations 5 and 6 was about 10 cm.

The flap 9 measured about 44 cm by 36 cm and was made of the same material as panels 2 through 4. The flap 9 was adhered to the reinforcing patch 7 by the same adhesive used to attach laterally extending panels 3 and 4 to central panel 2.

Modifications may be made in the invention without departing from the spirit of it. It will be understood by one skilled in the art that the dimensions and geometry of the drape itself, its fenestrations 5 and 6 and the flap 9 may be varied, depending upon the surgical procedure for which it is intended. The flap 9 need not be made of the same material as the remainder of the surgical drape. Furthermore, additional tape tab or other suitable means could be added to the flap 9 to secure the flap in its second position illustrated in FIG. 2.

What I claim is:

1. A surgical drape having first and second fenestrations formed therein, a flap hingedly affixed to said surgical drape between said first and second fenestrations, said flap being shiftable between a first position in which it covers and isolates said first fenestration and a second position in which it covers and isolates said second fenestration.

2. The structure claimed in claim 1 wherein said drape has a T-shaped configuration and comprises an elongated rectangular central panel and a pair of rectangular panels of lesser length, said panels of lesser length being affixed to either side of said central panel so as to extend laterally therefrom, said central panel having said first and second fenestrations formed therein.

3. The structure claimed in claim 2 including a reinforcing patch affixed to said central panel and surrounding said first and second fenestrations, said flap being hingedly affixed to said reinforcing patch between said fenestrations.

4. The structure claimed in claim 3 wherein said first and second fenestrations share a common centerline, said flap being hingedly affixed to said reinforcing patch between said fenestrations along a line perpendicular to said common centerline.

5. The structure claimed in claim 4 wherein said central panel, said laterally extending panels and said flap are made of disposable nonwoven fabric suitable for use in a surgical environment.

6. The structure claimed in claim 5 including means to releasably maintain said flap in said first position.

7. The structure claimed in claim 6 wherein said means to releasably maintain said flap in said first position comprises a tape tab attached to said flap.

8. The structure claimed in claim 1 wherein said first and second fenestrations share a common centerline, said flap being hingedly affixed to said drape between said fenestrations along a line perpendicular to said common centerline.

9. The structure claimed in claim 1 including a reinforcing patch affixed to said drape and surrounding said first and second fenestrations, said flap being hingedly affixed to said reinforcing patch between said fenestrations.

10. The structure claimed in claim 1 wherein said drape and said flap are made of disposable nonwoven fabric suitable for use in a surgical environment.

11. The structure claimed in claim 1 including means to releasably maintain said flap in said first position.

12. The structure claimed in claim 11 including a discardable fenestration control sheet located over said first fenestration and beneath said flap when said flap is initially in said first position.

13. The structure claimed in claim 5 including a discardable fenestration control sheet located over said first fenestration and beneath said flap when said flap is initially in said first position.

14. The structure claimed in claim 5 wherein said drape comprises a disposable laparoscopy drape, said first fenestration being so positioned in said central panel as to overlie a patient's abdominal area, and said second fenestration being so located in said central panel as to overlie the patient's perineal area.

* * * * *

Dedication 4,196,723.—*Lawrence A. Moose, Jr.*, Memphis, Tenn. DUAL FENESTRATED SURGICAL DRAPE WITH A FLAP CAPABLE OF COVERING AND ISOLATING EITHER FENESTRATION. Patent dated Apr. 8, 1980. Dedication filed Oct. 17, 1983, by the assignee, *Buckeye Cellulose Corp.*

Hereby dedicates to the Public the remaining term of said patent.
[*Official Gazette December 6, 1983.*]